United States Patent [19]
Jansen et al.

[11] Patent Number: 5,504,334
[45] Date of Patent: Apr. 2, 1996

[54] SIGNAL PROCESSING IN SCINTILLATION CAMERAS FOR NUCLEAR MEDICINE

[75] Inventors: Floribertus P. M. H. Jansen, Brookfield, Wis.; David M. Binnie, Sutton, England

[73] Assignee: General Electric Company, Milwaukee, Wis.

[21] Appl. No.: 258,015

[22] Filed: Jun. 10, 1994

[30] Foreign Application Priority Data

Jul. 12, 1993 [GB] United Kingdom ............... 9314398

[51] Int. Cl.⁶ .................................................. G01T 1/208
[52] U.S. Cl. ........................................ 250/369; 250/366
[58] Field of Search ................................. 250/369, 366

[56] References Cited

U.S. PATENT DOCUMENTS

| | | | |
|---|---|---|---|
| 4,228,515 | 10/1980 | Genna et al. | 364/571 |
| 4,475,042 | 10/1984 | Arseneau | 250/363 |
| 4,672,542 | 6/1987 | Roux et al. | 364/414 |
| 4,860,205 | 8/1989 | Jatteau | 364/413.24 |
| 4,881,171 | 11/1989 | Jatteau et al. | 364/413.24 |

FOREIGN PATENT DOCUMENTS

| | | | |
|---|---|---|---|
| 2600168 | 12/1987 | France. | |
| 59-60382 | 4/1984 | Japan | 250/369 |
| 1588921 | 4/1981 | United Kingdom. | |
| 1593426 | 7/1981 | United Kingdom. | |
| 2156177 | 10/1985 | United Kingdom. | |

*Primary Examiner*—Constantine Hannaher
*Attorney, Agent, or Firm*—Quarles & Brady

[57] ABSTRACT

In order to average out thermal noise but to magnify small value photon signals resulting from a gamma ray event in a scintillation camera having an array of photodetectors arranged in rows and column, the photon signals are summed for each row and summed for each column as a first step in the processing of the signals. As a second step the summed signals are weighted in accordance with an approximation to an energy distribution curve, and the weighted signals are then further weighted and summed for determining the position of the gamma ray event.

18 Claims, 5 Drawing Sheets

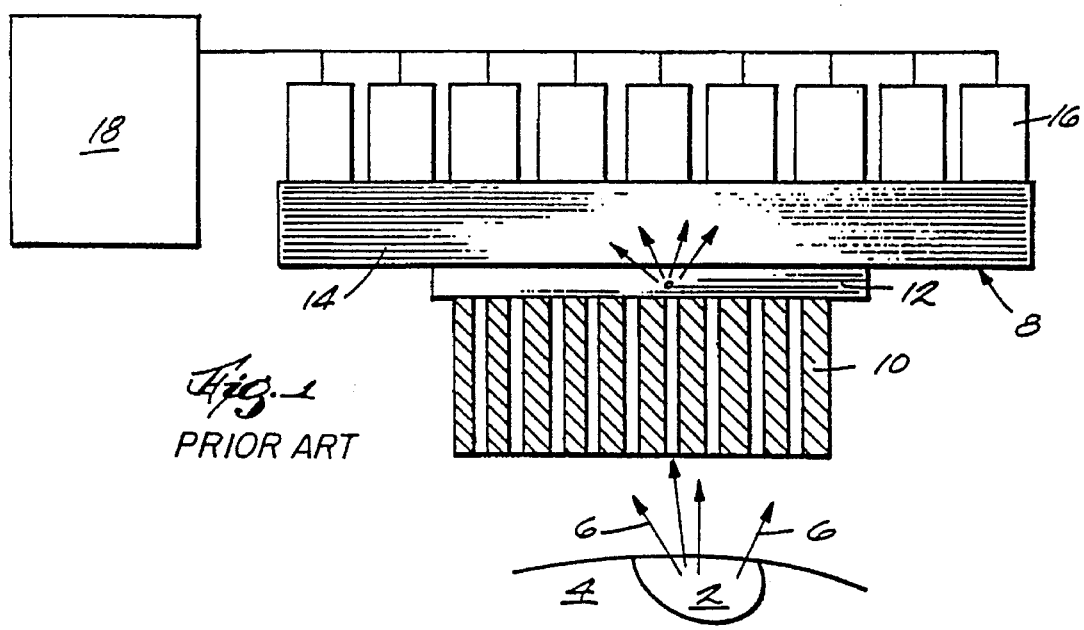
Fig. 1 PRIOR ART
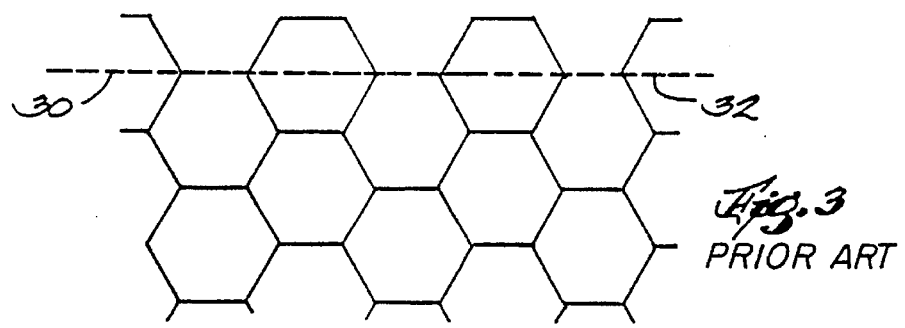
Fig. 3 PRIOR ART
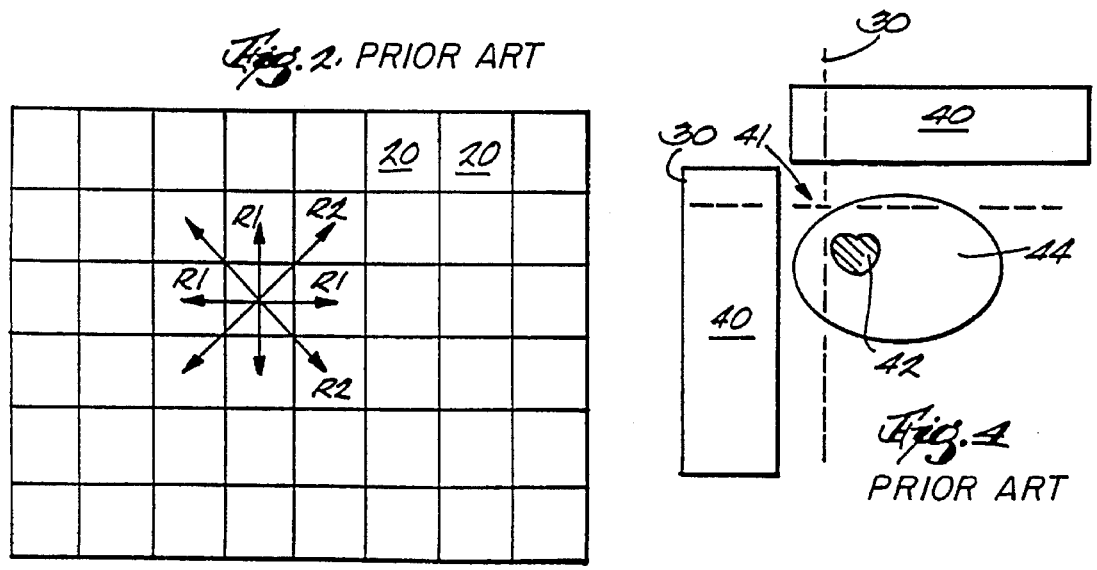
Fig. 2 PRIOR ART
Fig. 4 PRIOR ART 5,504,334

SIGNAL PROCESSING IN SCINTILLATION CAMERAS FOR NUCLEAR MEDICINE

FIELD OF THE INVENTION

The present invention relates to a method and apparatus for signal processing in scintillation cameras employed for nuclear medicine. Such scintillation cameras are also known as gamma cameras or Anger cameras and are more generally referred to as position and energy sensitive radiation detectors.

BACKGROUND ART

A common type of camera is shown in FIG. 1. An area (2) of a body (4) of a patient containing a radioactive pharmaceutical, emits gamma rays indicated as at (6). The camera (8) includes a collimator comprising an apertured lead sheet (10) so that only gamma rays within a predetermined narrow angle from the patient can pass through the collimator to a scintillation block (12) of NaI(T1). Single gamma rays entering block (12) give rise to a large number of secondary photons which radiate outwards through a glass light guide and support block (14) to an array of photomultipliers (16). Photomultipliers (16) are usually arranged in a rectangular or hexagonal grid. Each photomultiplier tube is arranged to detect individual photons or groups of photons to produce a significant electrical signal which is conducted to a signal processing unit (18). Unit (18) assesses all the signals received from the individual photomultiplier tubes to carry out an analysis of the signals received at consecutive time instants in order to determine approximately where each gamma ray impinges on scintillation block (12).

Position reconstruction in a gamma camera is usually performed by taking a linear weighted mean of the signals of the photomultiplier array, see for example US-A-4228315. Problems arise with signals from photomultipliers far from a gamma ray event where only a very small number of photons are detected. Since the statistical noise fluctuations are proportional to the square root of number of photons detected, the fluctuation in small signals is comparable to the signal itself. Because of this relatively large statistical noise fluctuation some form of limiting has to be applied to the smallest signals to exclude noise in order to obtain better spatial resolution. This may be done with a thresholding device, for example a diode, which provides a fixed thresholding level and which therefore only passes signals from a photomultiplier tube having a voltage level greater than the junction voltage of the diode. Whilst this provides a simple way of excluding low value signals which have a large amount of noise associated therewith, some useful information is also discarded. Now each gamma ray incident will create a distinctive energy dependent distribution curve of detected photons. Therefore, if a fixed threshold level is subtracted from each photomultiplier tube signal, the resulting distribution curve is effectively distorted during measurement and position reconstruction becomes inaccurate.

Referring now to FIG. 3, this shows a hexagonal array of close-packed photomultiplier tubes; this is a preferred configuration from the point of view of signal processing since the nearest neighbors of each tube are spaced the same distance R from the center of the tube as indicated in FIG. 3. This simplifies analog processing of the signals. However a problem arises with the hexagonal array in that at the edges of the array there are gaps as indicated in FIG. 3 in the region (30), which give rise to a reduced field of view indicated by the dotted line (32). This is a particular problem with arrangements such as shown in FIG. 4 wherein two cameras (40) are arranged at right-angles, contacting one another at their edges in order to get an improved view of a side region (42) of a patient's torso (44), for example the head. The result of the reduced field of view in the corner area is to create a dead region (46) for detection, with the result that the two cameras have to be positioned relatively far from the patient, resulting in a loss of resolution.

A preferred configuration which avoids the reduced field of view is to employ square photomultiplier tubes (20) arranged in a rectangular grid as shown in FIG. 2. In this arrangement the array extends right up to the edge of the camera. However, a disadvantage is that the nearest neighbors of each tube are spaced at various distances from the center of the tube as indicated by the dimensions R1 and R2 in FIG. 2. This places greater demands on analog signal processing required to identify the spatial location of a gamma ray incident. With a rectangular array therefore the noise effects and threshold effects are likely to be more pronounced. These effects will be exacerbated when large aperture photomultiplier tubes are employed for low cost. Clearly smaller photomultiplier tubes increase the overall resolution of the array, but larger tubes are preferred from the point of view of expense.

SUMMARY OF THE INVENTION

It is an object of the invention to reduce the above described problems of noise.

The present invention is based on the realization that there are two different types of noise encountered with scintillation cameras and that it is possible to discriminate between the two. The first type of noise is random noise, generated by photomultiplier dark current, amplifier noise, scintillator afterglow, etc. It is often referred to as thermal noise and contains no useful information. The second type of noise is small signal noise associated with the detection of a small number of photons far from the source; due to the statistical nature of the scintillation, the magnitude of these small signals will vary by an amount comparable to the magnitude of these signals, giving rise to apparent noise; however these signals do have a useful information content.

In accordance with the invention, signals from a row or column of a photodetector, e.g., photomultiplier array in a scintillation camera are summed or combined in some way before thresholding. This as will be shown will average out thermal or random noise, but will amplify small value photon signals which will occur coincident in time and can therefore be summed arithmetically to reduce the statistical fluctuation thereof.

The present invention thus provides a method of signal processing in a scintillation camera, the camera comprising a collimator adjacent a scintillation block which is optically coupled to an array of photodetectors, the array being distributed relative to two different axes to form rows and columns relative to the two axes, wherein the method comprises, for each row and for each column, summing or otherwise combining the output signals of the photodetectors of the respective row or column as a first step in the processing of the signals.

In a further aspect the invention provides a scintillation camera including a collimator adjacent a scintillation block which is optically coupled to an array of photodetectors, the array being distributed relative to two different axes to form rows and columns relative to the two axes, each photodetector having output port means providing an output signal, the output signals of each respective row or column being connected to a respective means for summing or otherwise combining the output signals whereby the output signals from each row and column are combined as a first step in signal processing.

The photodetectors may be of any well-known type, for example photomultiplier tubes or solid state detectors such as avalanche diodes or silicon diodes. The detectors may be used to detect single gamma ray events or more than one simultaneous event, as with position emission tomography.

The detectors may be arranged in any convenient array which is defined relative to two axes. Hexagonal and rectangular arrays have been descried above but others arrays may be envisaged, for example, a rectangular array where detectors in one row are staggered relative to detectors in adjacent rows.

In the camera according to the invention, the scintillation block will commonly be optically coupled to the array of photodetectors by a light guide, e.g., a glass block. However, with, for example, positron emission tomography, the light guide may be dispensed with.

The photodetectors will not normally have any signal processing elements contained within them and the output signal will be delivered in an unprocessed state at the output port. However each detecting element may include some linear processing, e.g., pre-amplification, integration or pulse shaping. In any event, the summing of the output signals will be in accordance with the invention the first signal processing step external to the photodetectors.

Each photodetector may include more than one output port. Thus where two dimensional position information is required a second output port will be provided providing a second output signal. In addition, for deriving a total energy signal from all of the detectors as is commonly required in signal processing, each detector may provide a third output signal at a third output port. Each output port is a separate source of signal energy and is adapted to provide a sufficient amount of energy for the desired purpose of summing a number of such signals at a common node. For example in the case of a photomultiplier tube, the tube includes a preamplifier providing an output voltage signal. A plurality of resistors are coupled to receive the output voltage and each provides a desired output current to a respective output port.

A second step in the processing of the output signals subsequent to summing, will normally be some type of thresholding or weighting. It is preferred in accordance with the invention to subject the summed output signals to a predetermined transfer function which linearizes the photon energy distribution curve. This will be described in more detail below.

In one arrangement the transfer function may comprise an attenuation value which is directly dependent on the total energy of the signals from all tubes and the individual signal. Thus the transfer function weights an input signal according to the degree of confidence one has in the input signal. Various other arrangements may be employed for weighting the summed input signals with a predetermined transfer function including digital arrangements.

The present invention lends itself to the application of digital electronics. Although digital electronics have been employed in prior arrangements, it has previously been necessary to provide a separate analog-to-digital converter for each photodetector. In accordance with the invention, however, in a digital implementation the number of ADCs may be drastically reduced since it is only necessary to have one ADC for each summed output signal of a respective row or column. Thus for example for a 6×8 array of photodetectors, it is only necessary to have 14 ADCs as opposed to prior arrangements of 48 ADCs. In addition, if very high speed ADCs are employed, it may be possible to sample the outputs of two or more rows or columns with a single multiplexing ADC.

Where ADCs are employed, conversion will take place subsequent to summing of the output signals and prior to thresholding or weighting of the output signals. A digital weighting transfer function may be implemented simply with a look-up table or through mathematical description.

Subsequent to weighting of the output signals, it is necessary to process the output signals to ascertain the position of an event. This is preferably done by linear weighting in predetermined manner of the row signals, summing the weighted signals and performing arithmetic computations as described below. A similar procedure is carried out for the column signals.

BRIEF DESCRIPTION OF THE DRAWINGS

A preferred embodiment of the invention will now be described with reference to the drawings wherein:

FIG. 1 is a schematic view of a known type of scintillation camera.

FIGS. 2 and 3 are schematic elevational views of rectangular and hexagonal arrays of photomultiplier tubes, respectively.

FIG. 4 is a schematic view of two cameras, each of a type shown in FIG. 1, arranged at right-angles for viewing a region, for example the heart, in a side region of a torso.

FIG. 7 is a schematic circuit diagram of an array of photomultipliers of a scintillation camera in accordance with a first embodiment of the invention including analog signal processing circuitry.

DESCRIPTION OF THE PREFERRED EMBODIMENT

Figure 5:
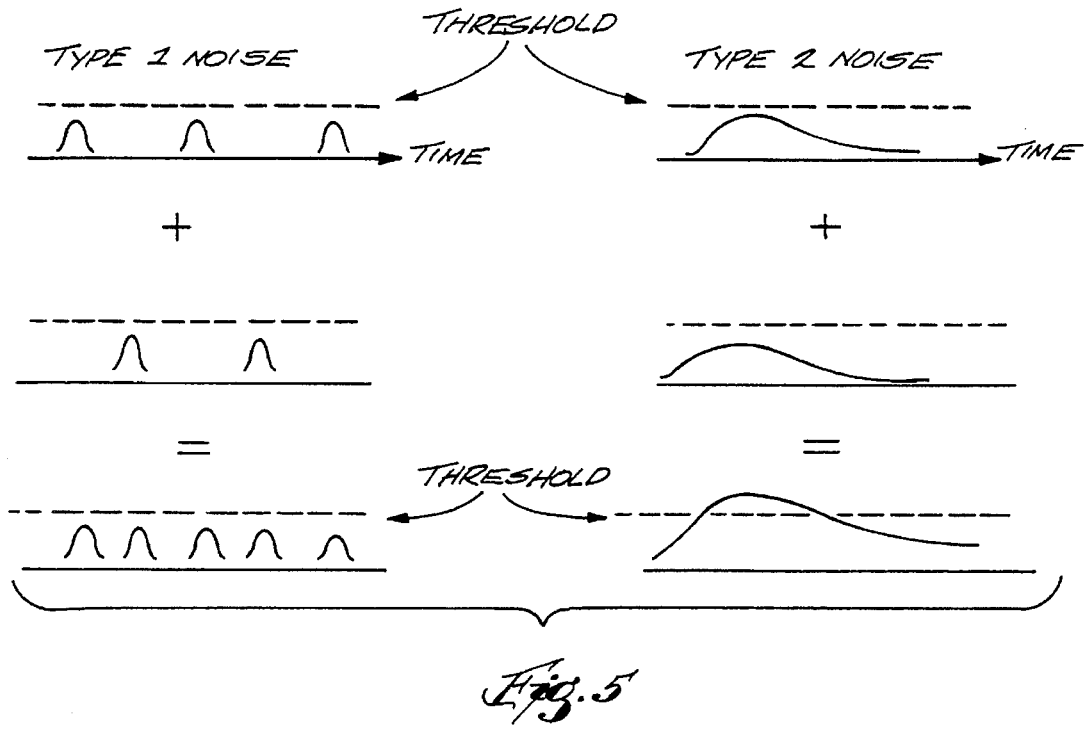
FIG. 5 is a schematic illustration of the concept which the present invention incorporates for reducing noise problems.

Referring now to FIG. 5, this illustrates the concept referred to above which is incorporated in the present invention for reducing noise problems.

It is important to distinguish between two different types of noise which thresholding attempts to deal with. Type 1 noise is random noise, generated by photomultiplier dark current, amplifier noise, or scintillator afterglow. This contains no useful information, and should always be discarded. Type 2 noise is small signal noise, associated with the detection of a small number of photons far from the source. Due to the statistical nature of the scintillation, the magnitude of these small signals will vary a lot, giving rise to apparent "noise." However, these signals do have a useful information content.

In the prior art the requirement for thresholding out noise of type 1 did not allow individual small signals to make any contribution to the position signal, as the individual small signals are insufficient to exceed the threshold. However, in accordance with the invention combining a number of these signals along a direction with equal information content (along a row or column) prior to thresholding gives a distinct advantage; where the signals contain position information, the fact that this will be highly correlated "noise" (type 2) which will be approximately coincident in time means the combined signal can exceed a threshold whereas uncorrelated noise (type 1) will not. Thus the rounding error associated with the assumption that all small signals are equal to zero (which is implied by thresholding them out completely) is removed (see FIGS. 1 and 2).

Figure 6:
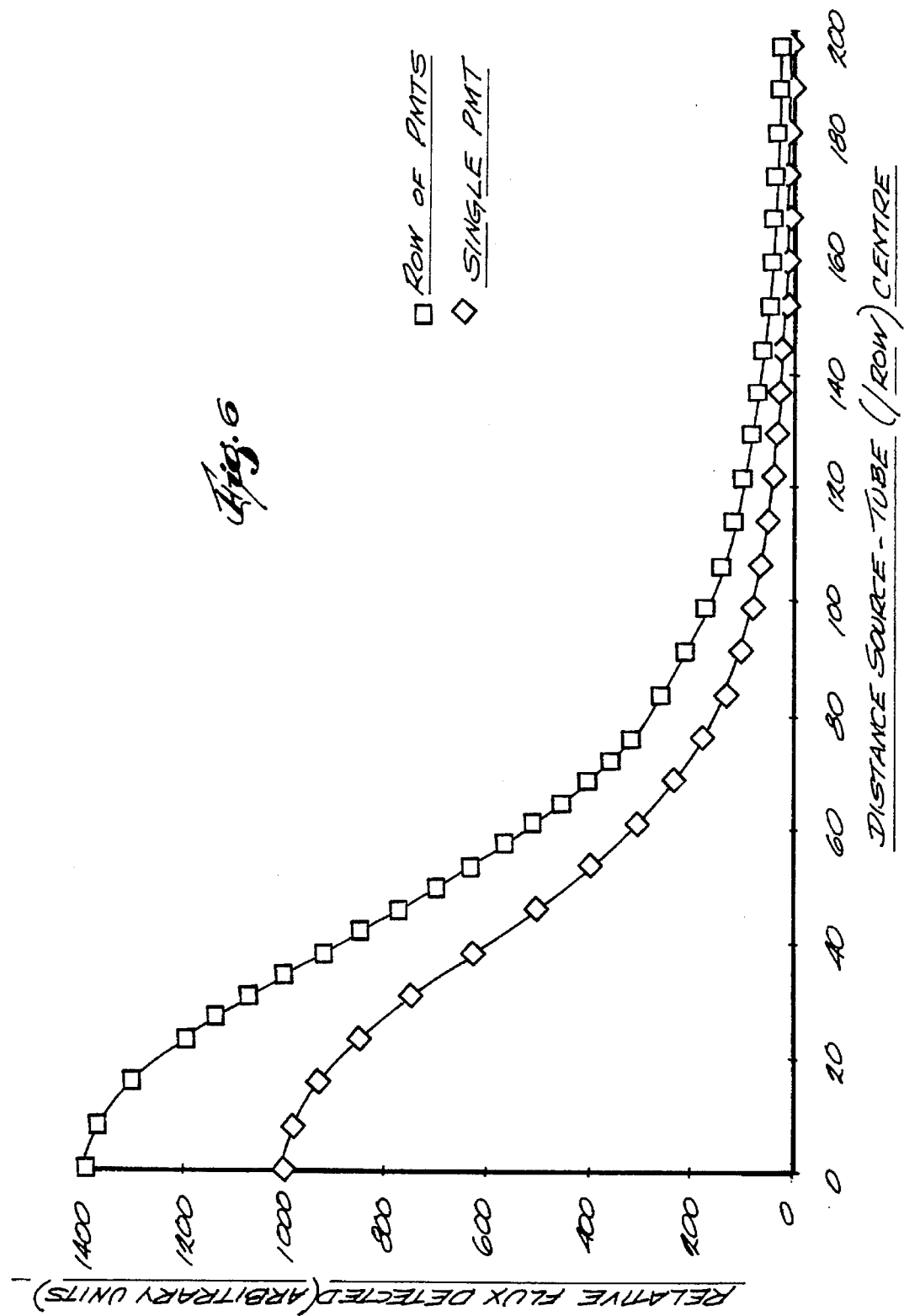
FIG. 6 is a scale diagram of the intensity distribution curve for photons detected from a gamma ray incident as measured in a direction across the camera.
Figure 5:
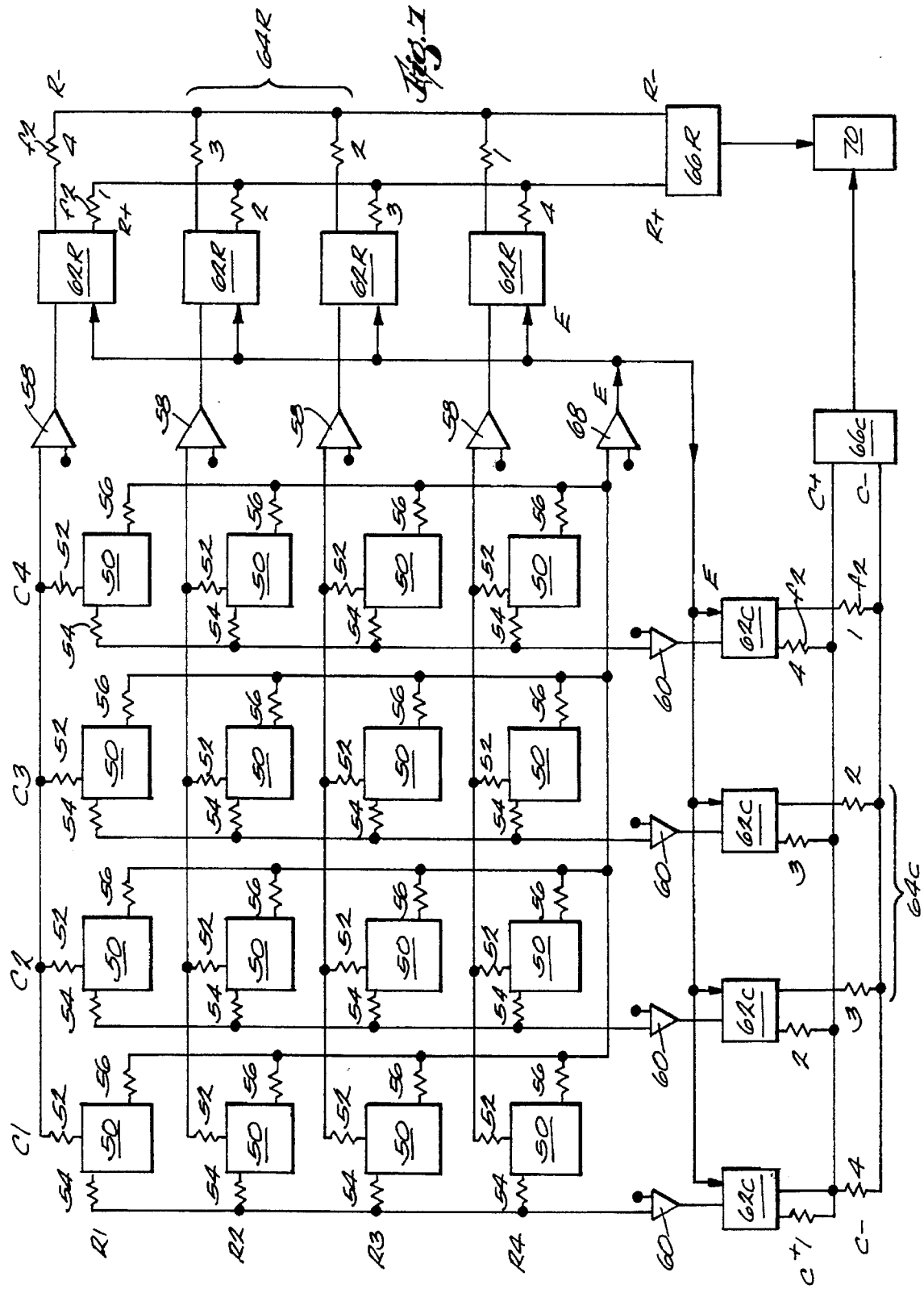

Referring now to FIG. 6 this shows to scale, a photon energy distribution curve for a single gamma ray event as detected by a single photomultiplier (line with diamonds) or row or column of photomultipliers (line with squares). In this figure the ordinate axis represents lateral displacement across camera width of the source of radiation with respect to the center of the photomultiplier row or column, in millimeters. It may be seen that at a source displacement of 76 mm (the edge of a photomultiplier tube) the total unthresholded signal detected in a row of photomultipliers is approximately 1.8 times greater than the signal on an individual tube.

Referring now to FIG. 7 a rectangular array of photomultipliers (50) is shown, each photomultiplier being of rectangular cross-section. The array shown is a 4×4 array although in a practical camera the array will be much larger, for example 6×8. Each photomultiplier has first, second and third output ports (52,54,56) respectively.

Each row of photomultipliers (R1,R2,R3 . . . etc.) have their first output ports (52) connected in common to a summing amplifier (58). Each column of photomultipliers (C1,C2,C3 . . . etc.) have their second output ports (54) connected in common to a summing amplifier (60). The output from each summing amplifier (58) is applied to a weighting transfer function device (62R), and the outputs from summing amplifiers (60) are applied to weighting transfer function devices (62C), described hereinafter in connection with FIG. 8. The output signals from devices (62R,C) are respectively applied to linear weighting networks (64R,64C) (described hereinafter) where the signals are combined in a predetermined manner and then processed in normalization units (66R,66C) (likewise described hereinafter).

The third output port (56) of each photomultiplier tube is summed in a summing amplifier (68) to provide a total energy signal E for a gamma ray event detected in the tubes. The output detected energy signal is applied to normalization units (66R,66C). In an alternative embodiment, this energy signal may be applied only to the transfer function devices (62R,C).

Figure 8A:
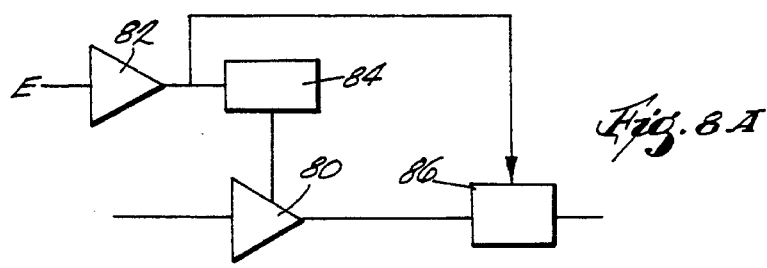
FIG. 8A is a schematic view of a circuit for generating a predetermined weighting transfer function to be applied to the sum output signals.

Referring now to FIG. 8A, a weighting transfer function device (62,R,C) is shown in more detail as comprising a variable gain amplifier (80) whose gain is determined by the total energy signal E applied via a buffer amplifier (82) and a unit (84) to the variable gain input of amplifier (80). It may be seen from FIG. 7 that the other input to amplifier (80) in the output of a summary amplifier (58) or (60). Unit (84) is a translating unit, that is, a device that translates upward or downward the signal input to amplifier 80. In addition a non-linear element (86) is provided in the output signal path of amplifier (80) whose impedance is determined by the total energy signal. The nonlinear element (86) may for example comprise a transistor.

Figure 8B:
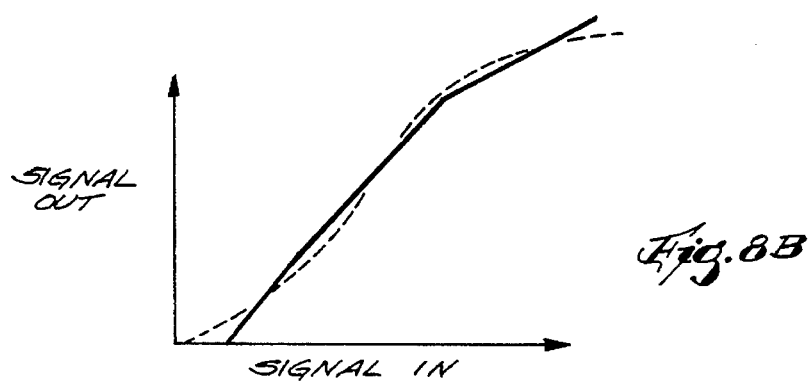
FIG. 8B is a graph showing the transfer function generated.

As indicated in FIG. 8B the characteristics of amplifier (80) and non-linear element (86) are so determined as to provide the transfer function illustrated. The transfer function actually provided by the device (62,R,C) is depicted by a solid line comprising an initial state representing a variable threshold level followed by a straight line curve, the slope of the curve depending on the total energy, followed by a straight line of smaller slope for high value input signals. The two straight line slopes are provided by unit (84). It may be seen this transfer function is an approximation to an ideal energy distribution curve, which is indicated in dotted lines, and thus provides a weighting to the output signal which takes due account of the statistical noise value in the signal.

The output signals from the thresholding devices (62R) are applied to a resistive network (64R) where the signals are linearly weighted in the ratios indicated by impedances 72 and then added in two sets $R^+$ and $R^-$. For the four resistors of each set, the ratios between respective resistances are designated by the numerals 1–4 shown in FIG. 7. A similar network (64C) is provided for the output column signals where the signals are weighted and added in two sets $C^+$, $C^-$. It will be noted that the conductance value of the impedances (72) in the two sets change linearly and stepwise from one side of the array of tubes to the other. This represents a position dependent weighting and enables the position of the gamma ray event within the row or column to be computed in normalization units (66,R,C) from the following equation:

$$\frac{\Sigma S_i x_i}{\Sigma S_i}$$

where $S_i$ represents the total energy of the output signals from the devices (62R,C) for a row or column, and $X_i$ represents the position of the tube in the row or column. The units 66R and 66C thus comprise any computational device available for making the above normalization calculation.

Thus at this point the position of a gamma ray event detected by the camera is known in terms of its position and its total energy. This essentially fully characterizes the signal for further processing in a digital signal processing unit (70).

Figure 9:
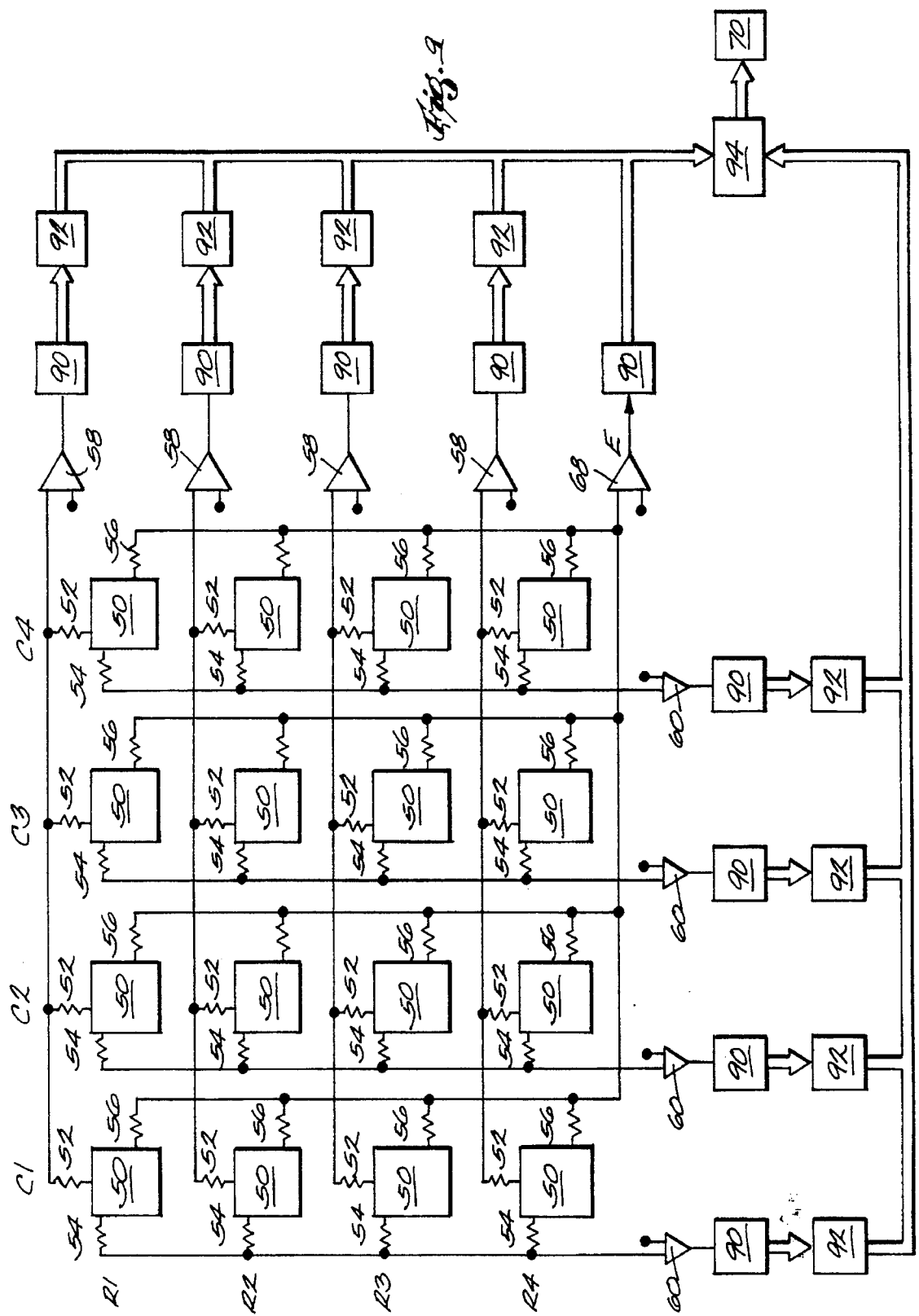
FIG. 9 is a schematic circuit diagram of a scintillation camera in accordance with a second embodiment of the invention including digital processing circuitry.

Referring now to FIG. 9 a second embodiment of the invention is shown wherein the same reference numeral is employed for that shown in FIG. 7. The principal difference is that following summation of the rows and column signals the signals are digitized in ADC units (90) and are then applied to digital versions of weighting transfer function devices (92). Following weighting, the signals are normalized by a microprocessor unit (94) in order to provide the above normalization equation.

What is claimed is:

1. A method of signal processing in a scintillation camera, the camera comprising a collimator adjacent a scintillation block which is optically coupled to an array of photodetectors, the array being distributed relative to two different axes to form rows and columns relative to the two axes, wherein the method comprises for each row combining the output signals of the photodetectors to provide a corresponding summed signal, and for each column, combining the output signals of the photodetectors to provide a corresponding summed signal for each column, as a first step in signal processing, wherein each photodetector provides a first output for row summation and a second output for column summation.

2. A method of signal processing in a scintillation camera, the camera comprising a collimator adjacent a scintillation block which is optically coupled to an array of photodetectors, the array being distributed relative to two different axes to form rows and columns relative to the two axes, wherein the method comprises, for each row and for each column, summing or otherwise combining the output signals of the photodetectors of the respective row or column to provide a corresponding summed signal, as a first step in signal processing, wherein in a second step the summed signals of respective rows and columns are weighted in accordance with their relative amplitude.

3. A method according to claim 2 wherein the summed signals are weighted in accordance with their amplitude relative to a total energy signal.

4. A method as claimed in claim 3 wherein the summed signals are .weighted by an amount in accordance with a predetermined distribution curve.

5. A method of signal processing in a scintillation camera, the camera comprising a collimator adjacent a scintillation block which is optically coupled to an array of photodetectors, the array being distributed relative to two different axes to form rows and columns relative to the two axes, wherein the method comprises, for each row and for each column, summing or otherwise combining the output signals of the photodetectors of the respective row or column to provide a corresponding summed signal, as a first step in signal processing, wherein all of the summed row signals and all of the summed column signals are respectively subjected to a linear weighting and summing procedure to determine the position of a gamma ray event.

6. A scintillation camera including a collimator adjacent a scintillation block which is optically coupled to an array of photodetectors, the array being distributed relative to two different axes to form rows and columns relative to the two axes, each photodetector having output port means providing first and second output signals, the output ports of the photodetectors in each respective row being connected to a respective means for summing or otherwise combining the first output signals, the output ports of the photodetectors in each respective column being connected to a respective means for summing or otherwise combining the second output signals whereby the output signals are combined as a first step in signal processing.

7. A camera according to claim 6 including row position determination means and column position determination means being respectively coupled to receive all the summed row signals and all the summed column signals for deriving a signal indicative of a gamma ray event position relative to the rows or columns, respectively.

8. A camera according to claim 6 including analog to digital conversion means coupled to receive the output of each summing means.

9. A camera according to claim 6 wherein the output from the summing means is applied to a weighting means which subjects the summing means output to a predetermined transfer function.

10. A camera according to claim 9 including means for determining a total energy signal from the output signal of the photodetectors and wherein the weighting means is arranged to provide a variable degree of amplification/attenuation in dependence on the value of said total energy signal.

11. A camera according to claim 10 including row position determination means and column position determination means being respectively coupled to receive all the summed row signals and all the summed column signals for deriving a signal indicative of a gamma ray event position relative to the rows or columns, respectively.

12. A camera according to claim 9 including row position determination means and column position determination means being respectively coupled to receive all the summed row signals and all the summed column signals for deriving a signal indicative of a gamma ray event position relative to the rows or columns, respectively.

13. A camera according to claim 6 including row position determination means and column position determination means being respectively coupled to receive all the summed row signals and all the summed column signals for deriving a signal indicative of a gamma ray event position relative to the rows or columns, respectively.

14. A camera according to claim 13 wherein each position determination means includes an impedance network for linearly weighting in predetermined manner the summed row or column signals and summing such linearly weighting signals, and means for performing arithmetic computations on such summed signals.

15. A scintillation camera comprising a collimator adjacent a scintillation block which is optically coupled to an array of photodetectors, wherein:

said photodetector array comprises a plurality of square photomultiplier tubes, said photomultiplier tubes are arranged in a rectangular grid to form rows and columns relative to two non-parallel axes, said photomultipliers respectively providing output signals;

a row summing means corresponding to each photomultiplier row, each row summing means receiving an output signal from each photomultiplier in its corresponding row to provide a summed row signal;

a column summing means corresponding to each photomultiplier column, each column summing means receiving an output signal from each photomultiplier in its corresponding column to provide a summed column signal; and means for receiving said summed row signals and summed column signals for selectively weighting said received signals to provide an output representing the position of a gamma ray event.

16. The camera of claim 15 wherein each of said summed signals received by said weighting means is weighted in accordance with its relative amplitude.

17. The camera of claim 15 wherein each of said summed signals received by the weighting means is weighted in accordance with its amplitude relative to a signal representing the total energy cumulatively detected by all the photomultipliers in the array in response to a gamma ray event.

18. The camera of claim 15 wherein said weighting means comprises means for weighting each of said summed signals in accordance with the position in the array of the row or column to which the summed signal corresponds.

* * * * *